United States Patent [19]

Connery et al.

[11] Patent Number: 4,879,517
[45] Date of Patent: Nov. 7, 1989

[54] TEMPERATURE COMPENSATION FOR POTENTIOMETRICALLY OPERATED ISFETS

[75] Inventors: James G. Connery, Ambler; Earl W. Shaffer, Jr., Lansdale, both of Pa.

[73] Assignee: General Signal Corporation, Stamford, Conn.

[21] Appl. No.: 224,510

[22] Filed: Jul. 25, 1988

[51] Int. Cl.$^4$ .............................................. G01N 27/56
[52] U.S. Cl. .................................. 324/438; 324/71.5; 204/406
[58] Field of Search ....................... 324/765, 438, 441; 204/1 T, 408, 433, 416

[56] References Cited

U.S. PATENT DOCUMENTS

| 4,385,274 | 5/1983 | Shimada et al. | 324/71.6 |
| 4,490,678 | 12/1984 | Kuisl et al. | 324/438 |
| 4,505,799 | 3/1985 | Baxter | 204/416 |
| 4,589,970 | 5/1986 | Ligtenberg et al. | 204/416 |
| 4,641,249 | 2/1987 | Gion et al. | 324/438 |
| 4,657,658 | 4/1987 | Sibbald | 324/71.6 |
| 4,691,167 | 9/1987 | Vlekkert et al. | 324/71.6 |
| 4,701,253 | 10/1987 | Ligtenberg et al. | 204/416 |

FOREIGN PATENT DOCUMENTS 80402 11/1981 European Pat. Off. ............ 324/438

OTHER PUBLICATIONS

P. Bergveld, The Operation of an ISFET as an Electronic Device, Sensors and Actuators 1, (1981), pp. 17–29.
A. Sibbald, A Chemical-Sensitive Integrated-Circuit: The Operational Transducer, Sensors and Actuators, 7,(1985), pp/23–38.
S. D. Moss, C. C. Johnson and Jiri Janata, Hydrogen, Calcium, and Potassium Ion-Sensitive FET Transducers: A Preliminary Report, IEEE Transactions on Biomedical Engineering, vol. BME-25, No. 1, Jan. 1978.

Primary Examiner—Reinhard J. Eisenzopf
Assistant Examiner—Maura K. Regan
Attorney, Agent, or Firm—William G. Miller, Jr.; Harold Huberfeld

[57] ABSTRACT

Compensation for the temperature sensitivity of the output of a potentiometrically operated ISFET probe whose drain-source voltage and drain-source current are held constant is provided by using a Nernstian temperature correction of the difference between the ISFET output and the isopotential voltage of the probe and offsetting the resulting difference by the isopotential pIon value. An ISFET/NISFET pair provides a cancellation of variations due to manufacturing.

20 Claims, 2 Drawing Sheets

TEMPERATURE COMPENSATION FOR POTENTIOMETRICALLY OPERATED ISFETS

BACKGROUND OF THE INVENTION

This invention relates to a method and means for providing temperature compensation for measurements made with potentiometrically operated ion-selective (sensitive) field effect transistor (ISFET) probe assemblies operating at temperatures other than the calibration temperature.

For many years glass electrode probe assemblies which are selective to hydrogen ions have been used to measure pH. It is well known that these elecrode assemblies are temperature sensitive so that their output must be compensated for the temperature of th solution being measured. The following relationships describe the temperature sensitivity of such electrode assemblies:

$$E = \frac{RT\ln 10}{F}((7 \pm \text{Std.}) - \text{pH}) \quad (1)$$

and $$\text{pH} = (7 \pm \text{Std.}) - \frac{F}{RT\ln 10} E, \quad (2)$$

where pH is the indicated or displayed value, Std. represents the standardization (calibration) value, $R\ln 10/F$ is the Nernst factor, T is the absolute temperature, R is the universal gas constant, F is Faraday's constant and E is the glass electrode-reference electrode voltage. The number 7 represents the isopotential pH for the glass electrode system, which is that pH value at which the electrode output is independent of temperature. At that pH value the output for the glass electrode system is zero volts, which is the isopotential voltage.

Typically, the correction of these electrodes for their temperature sensitivity involves only correction for the glass-electrolyte interfaces by adjustment of the amplification of the instrument measuring the voltage E in accordance with the Nernst factor with the temperature component of that factor being measured by a separate sensor. The temperature sensitivity of other elements of these probes, such as the external reference electrode, is cancelled out due to the fact that there is an opposing internal reference electrode as part of the glass electrode assembly.

In 1970 P. Bergveld developed the ion-selective field effect transistor (ISFET) which can be used to measure pH in place of the glass electrode. Such a transducer is basically a metal oxide semiconductor field effect (MOSFET) device whose construction differs from the conventional MOSFET devices in that the gate metal is omitted and special techniques are employed to render the gate region selective to the ions of interest. An example of a method which can be used to construct a suitable ISFET is described in U.S. Pat. No. 4,505,799, issued to Ronald D. Baxter, a coworker of mine, on Mar. 19, 1985.

In Bergveld's article, THE OPERATION OF AN ISFET AS AN ELECTRONIC DEVICE, Sensors and Actuators, 1 (1981) 17-29, he discusses the temperature sensitivity of ISFETs. He points out that the temperature drift of ISFETs involves problems beyond those encountered with glass electrodes since the reference electrode voltage and the standard potential of the electrolyte-oxide interface are variable with temperature as are certain solid state parameters. He also states, "A usual approach in electronics to compensate for temperature drift in solid-state devices is to create a differential pair on one chip from which one device is the active input device and the other is used for temperature compensation, assuming the temperature characteristics of both devices are equal." As he further states, "Both requirements can be met reasonably for a pair of MOSFETs with today's MOSFET technology and the application of electronic feedback . . . . It is, however not realistic to use this approach for a pair consisting of an ISFET and A MOSFET on the same chip . . . . " He goes on to describe his suggested approach to temperature compensation as one involving a pair of ISFETs, one for measuring pH and one with a separate compartment on top of the gate, filled with a buffered agarose, which is in contact with the solution to be measured via a liquid junction. He then sets forth the problems with that type of arrangement and concludes as follows: "The conclusion is that the approach of a differential pair construction on one chip to prevent temperature drift, as commonly in use for MOSFETs, cannot be applied directly to ISFETs." He also concludes that " . . . the simultaneous measurement of the temperature with a separate sensor cannot be used for compensation of temperature drift in $V_g(T)$ for $I_d$=constant. Instead of this, we have continuously to measure the unknown function for each individual ISFET connected to the amplifier during operation. With this measure, the set value of $I_d$ can be controlled in such a way that $V_g$=constant. The same signal can be used to adjust the amplification of the measured output signal as a function of pH, in agreement with the slope correction of glass membrane electrodes." The author also states that " . . . the temperature compensation mentioned above . . . does not correct changes in the voltage of the reference electrode . . . and the electrolyte-oxide standard potential . . . as a function of the temperature." It is, of course, important to provide for compensation for the temperature sensitivity of the reference electrode in order to have complete temperature compensation for the ISFET measurement. Thus, Bergveld's comments indicate that he did not know how to accomplish a complete temperature compensation of the ISFET.

In a paper entitled A CHEMICAL-SENSITIVE INTEGRATED-CIRCUIT: THE OPERATIONAL TRANSDUCER, published in Sensors and Actuators, 7 (1985) 23-38, the author, A Sibbald, outlines the three principal attempts which had been made previously to negate thermal sensitivity, as follows:

(1) Operation at a fixed, athermal $I_d$ (a locus in the $I_d/V_{gs}$ characteristic where the thermal effects are virtually self cancelling).

(2) A.C. signal injection technique which involves the injection of a high frequency signal into the ChemFET bulk with discrimination between the a.c. and d.c. components of the device output signal and thereby deriving separate signals related to chemical activity and to temperature.

(3) On-chip reference electrode. This electrode uses a pair of ChemFETs fabricated on the same chip such that the surface of one device is coated with a buffered 1% agarose gel and then encapsulated using epoxy, with a glass microcapillary forming a liquid-junction through the epoxy between the gel and the ambient thus providing a pH insensitive device and an adjacent pH sensitive device. A differential amplifier is then used for the measurement.

This author, in stating that he uses an array of ChemFETs operated at or near the athermal $I_d$ value, also indicated that it is nevertheless necessary to incorporate a miniature heat exchanger in the analysis system in order to minimize thermal effects and that it is essential that the threshold voltages of the individual ChemFet devices in the array are similar, which cannot be always guaranteed. He has thus indicated that no satisfactory, simple temperature compensation system had been devised when he wrote the paper.

It is amply evident from the above that temperature compensation of ISFETs, as practiced before the present invention, has either failed completely or required cumbersome systems, such as miniature heat exchangers. This has been so because ISFET assemblies exhibit three temperature sensitivities instead of one, as with the glass electrode. One is the Nernst temperature sensitivity, similar to that described above for the glass electrode. A second is the temperature sensitivity of the field effect transistor (FET) portion of the assembly. The third is the temperature sensitivity of the single reference electrode in the assembly.

In addition to the temperature sensitivity of the FET portion of the assembly, it has been found that current methods of semiconductor fabrication may lead to variations of the isopotential voltage of an ISFET assembly in excess of 20 mv. Such variations have been found to have the effect of limiting the accuracy of temperature compensation in systems where the ISFETs must be interchangeable. For example, it has been found that deviations of the isopotential voltage must be kept within a range of plus or minus 20 mv. in order to obtain an accuracy to 0.1 pH at any pH, over a temperature range of 0°–100° C.

It is an object of this invention to provide a method and means for compensating for the temperature sensitivity of all components of the ISFET assembly without using complicated circuits and without the need for complicated structure.

It is also an object of this invention to provide a method and means for overcoming the inaccuracies in temperature compensation in systems using interchangeable ISFETs as may be introduced by variations in semiconductor fabrication.

SUMMARY OF THE INVENTION

There is provided a method and means for compensating for the temperature sensitivity of the output of a potentiometrically operated ISFET probe whose drain-source voltage and drain-source current are held constant. This method and means provides a Nernstian compensation of the difference between the isopotential reference-to-source voltage and the ISFET output, whose result is offset by the isopotential value for the activity of the ion being sampled.

For accuracy in temperature compensation of systems using interchangeable production ISFETs, a non ion-selective FET (NISFET) constructed on the same substrate as the ISFET and simultaneously with the ISFET is arranged to have its output subtracted from the output of the ISFET before the above mentioned Nernstian compensation and isopotential offset are carried out.

DESCRIPTION OF THE PREFERRED EMBODIMENTS

Figure 1:
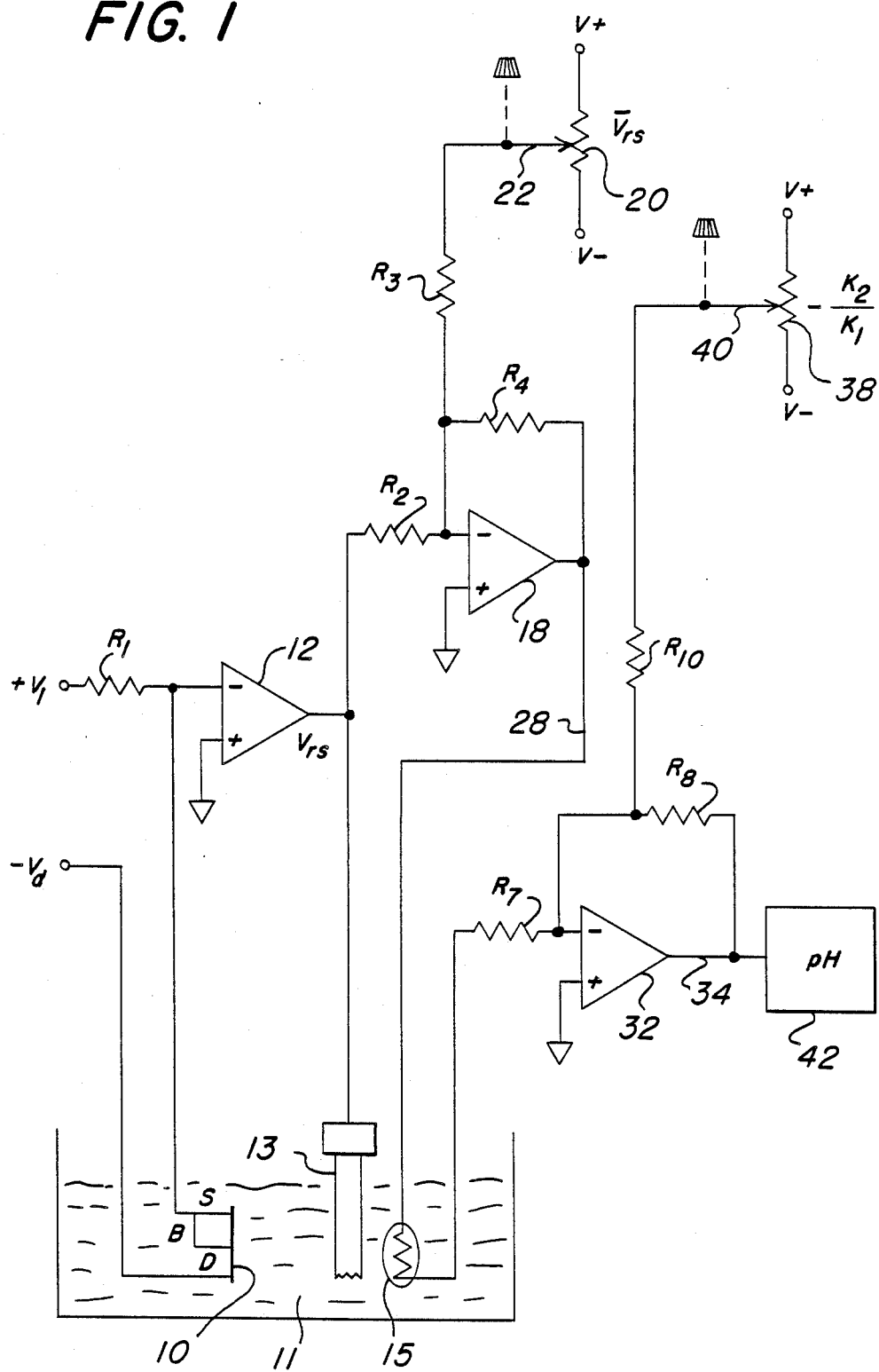
FIG. 1 is a circuit diagram for a p-channel enhancement mode ISFET pH device employing the temperature compensation of this invention using an RTD temperature sensor to sense the sample temperature.

For the purposes of this specification and the appended claims, it will be assumed that the term ISFET probe is taken to mean the ISFET itself in combination with the circuitry associated with the ISFET to provide an output signal related to the ionic activity of an electrolye sample in which it is immersed, including the requisite biases for its electrodes in order to obtain the desired mode of operation, such as for constant drain-source voltage and constant drain-source current, and the term ISFET probe assembly will include not only the ISFET probe but also the other elements which are immersed in the electrolyte sample in order to obtain the desired measurement and provide the necessary temperature compensation of that measurement.

With that assumption the output of an ISFET probe may be described by a first order equation relating measured voltage output of the ISFET probe, pIon, and the temperature of the electrolyte being measured. That relationship is:

$$V_{rs} = \overline{V}_{rs} + K_1(pIon)T + K_2T, \tag{3}$$

where $V_{rs}$ is the probe reference-to-source voltage. $\overline{V}_{rs}$ is the isopotential reference-to-source voltage, or the probe output at 0° K. $K_1$ is a constant, known as the Nernst factor, which is:

$$K_1 = \frac{R \ln 10}{zF} \tag{4}$$

where R is the universal gas constant, F is the Faraday constant and z is a function of ion charge. Continuing in equation (3), T is the absolute temperature and $K_2$ is the temperature coefficient of probe potentials other than (1) the potential at the interface between the ion-selective membrane of the ISFET and the electrolyte being measured, or (2) the in-situ temperature coefficient of the sample's ionic activity. pIon is defined as:

$$pIon = -\log_{10}(a_i) \tag{5}$$

where $a_i$ is the activity of the ion of interest. When $a_i$ describes the activity of the hydrogen or hydronium ion, then $$z = 1, \text{ and}$$

$$pIon = pH = -\log_{10}(a_{H^+}) \tag{6}$$

For the purpose of the subsequent description, it is assumed that the ion of interest is the hydrogen ion. In that case the fully temperature compensated pH of the sample under test can be determined from (3) as $$(pH) = \frac{(V_{rs} - \overline{V}_{rs})}{K_1 T} - \frac{K_2}{K_1}. \tag{7}$$

If the probe is immersed in a real or calculated solution of pH such that the observed voltage $V_{rs}=\overline{V}_{rs}$, the isopotential voltage, then pH$=-K_2/K_1$, which is the probe's isopotential pH.

Because probe output $V_{rs}$, $K_1$, and temperature T are known quantities, the determination of sample pH demands the additional knowledge of probe parameters $\overline{V}_{rs}$ and $K_2$. Since:

$$V_{rs}-K_1(pH)T=\overline{V}_{rs}+K_2T \tag{8}$$

we can plot $[V_{rs}-K_1(pH)T]$ vs. T. The slope of the plotted line is then $K_2$ and the intercept is $\overline{V}_{rs}$. Now, knowing the parameters $K_2$ and $\overline{V}_{rs}$, all parameters are known to fully determine and temperature compensate for measurement of an unknown pH sample by equation (7).

In the circuit of the FIG. 1 the ISFET 10 has its source connected to the inverting input of operational amplifier 12 and to a voltage source $+V_1$ through resistor $R_1$ so that the magnitude of the drain-source current will be controlled at $V_1/R_1$. A voltage source $-V_d$ is connected to the drain of ISFET 10 to control the drain-source voltage at a preselected level.

As is also shown in the FIG. 1, the output of amplifier 12 is connected to a reference electrode 13 so that the amplifier will drive the potential of the source of ISFET 10 to circuit common potential, for that is the potential at the non-inverting input of the amplifier. The output of amplifier 12 is the probe output $V_{rs}$.

In addition to the ISFET probe and the reference electrode, the probe assembly in FIG. 1 includes a resistance thermometer detector (RTD), 15, whose resistance varies with temperature.

From equation (7) it is evident that the measurement of pH by an ISFET such as 10 can be accomplished by first subtracting from the ISFET probe output $V_{rs}$ the quantity $\overline{V}_{rs}$, as determined, for example, from the plotting previously mentioned. That is followed by compensation for the Nernstian characteristics of the ISFET by dividing the difference obtained from the subtraction by the term $K_1T$, the Nernst factor times the absolute temperature. After the Nernstian compensation is accomplished it is necessary to offset or standardize for the isopotential value $K_2/K_1$. While these are known quantities, this term can be advantageously taken care of by the standardization process before the measurement is made. The standardization process will additionally take care of any residual offsets.

The quantity $\overline{V}_{rs}$ can be subtrated from the probe output $V_{rs}$ by the operational amplifier 18 and its associated circuitry, which includes resistors $R_2$, $R_3$, $R_4$, and the potentiometer 20, which is shown as being supplied from a voltage source spanning stable voltages $+V$ and $-V$ and having an associated manually adjusted tap 22. The signal to the inverting input of amplifier 18 is taken from the output, $V_{rs}$, of operational amplifier 12 by way of the input resistor $R_2$. The output of the amplifier 18 is then connected by way of feedback resistor $R_4$ to the inverting input to provide negative feedback. Also, the tap 22 of potentiometer 20 is connected to the inverting input of amplifier 18 through resistor $R_3$.

Appropriate values for resistors $R_2$, $R_3$, and $R_4$ will effectively cause the amplifier to subtract the quantity $\overline{V}_{rs}$ from the input signal $V_{rs}$, providing tap 22 is adjusted to provide a voltage at the tap such that the current in resistor $R_3$ will be representative of $-\overline{V}_{rs}$.

The output of amplifier 18 on line 28 is then representative of $(V_{rs}-\overline{V}_{rs})$.

It is next necessary to take care of the Nernstian compensation required by essentially dividing the output of amplifier 18 by the term $K_1T$. Nernstian compensation is well known in the glass electrode art, and is normally carried out by off-the-shelf pH measuring instruments. However, since the isopotential pH of an ISFET is not necessarily 8 and the corresponding isopotential voltage is not zero, the pH measuring instruments for glass electrodes can not normally be used to measure the pH with an ISFET.

FIG. 1 shows a simple circuit for taking into account the temperature compensation required for an ISFET. This circuit includes the resistance thermometer detector, RTD, 15, which is a resistance element whose resistance changes in a known fashion with changes in its temperature. The RTD is immersed in the sample being measured, as shown in the drawing, and is connected with resistor $R_7$ in a series circuit connecting the output of amplifier 18 on line 28 to the inverting input of operational amplifier 32. The non-inverting input of amplifier 32 is connected to circuit common and the amplifier's output is connected in a negative feedback path including resistor $R_8$ to the amplifier's inverting input. By virtue of these connections, an appropriate selection of values for resistors $R_7$ and RTD 15 so that their sum varies in direct proportion to the absolute temperature, and with an appropriate selection of the value for $R_8$, as well; the gain of amplifier 32 will vary as a function of the absolute temperature and the Nernst factor.

The signal outputted to line 34 from amplifier 32 must have a voltage added to it which represents the isopotential pH, $-K_2/K_1$. For this purpose there is provided another input to amplifier 32 which involves resistor $R_{10}$, and the potentiometer 38 with its tap 40, all of which are similar to amplifier 18 and its associated circuitry, and therefore also performs a subtracting function; namely, by the adding of the negative value of the ratio, $K_2/K_1$. The output of amplifier 32 is then a voltage which can be measured by an output device 42 as an indication of the pH measured by ISFET 10, providing the tap 40 is set to supply a potential which will produce a current in resistor $R_{10}$, representing $-K_2/K_1$.

It is evident that the tap 40 merely performs the function of a standardizing potentiometer. Thus, the tap 40 can be set by inserting the probe into a standard buffer solution and adjusting the tap 40 until the correct reading is obtained. By so doing, the isopotential pH will be taken care of along with any non-pH potentials in the circuit, which might otherwise cause an offset error.

While FIG. 1, as described, can be used to measure pH with an ISFET in such a way that the measurement will be independent of the temperature coefficients of the reference electrode and the FET structure, certain contributions to the term $\overline{V}_{rs}$ are expected to vary from ISFET to ISFET by as much as 500 mv. To achieve compensation to 0.1 pH over a useful temperature range, $\overline{V}_{rs}$ must be known to 20 mv. Because a multiplicity of ISFETs cannot now be made to a 20 mv. tolerance using standard manufacturing techniques, the fabrication and use of a companion FET is a useful way of compensating for such variations. Such an FET would not be ion-selective, what we are calling here a NISFET (non-selective field effect transistor), and would advantageously be made at the same time as the ISFET so as to assure that it would have the same characteristics, and therefore would be useful to cancel out manufacturing variations. Furthermore, the close physical proximity of the ISFET and the companion NISFET will assure that they are at the same temperature.

It is, of course, only necessary that the isopotential characteristics of the paired FETs match within the 20 mv. tolerance in order to obviate the need for individual temperature testing of the ISFETs in production. The NISFET can be a MOSFET or any other non ion-selective FET, such as those commonly known as REFETs (reference electrode field effect transistors). The differential ISFET vs. NISFET structure would follow functionally equation (3), even though different values of $\overline{V}_{rs}$ and $K_2$ may be obtained. Therefore, the temperature compensation set forth above for the ISFET would also work for an ISFET/NISFET pair, where its drain-to-source current and the drain-to-source voltage are also held constant. It is thus only necessary to set up the ISFET and NISFET as a differential pair in the circuit like that of FIG. 1. This has been done in FIG. 2.

Figure 2:
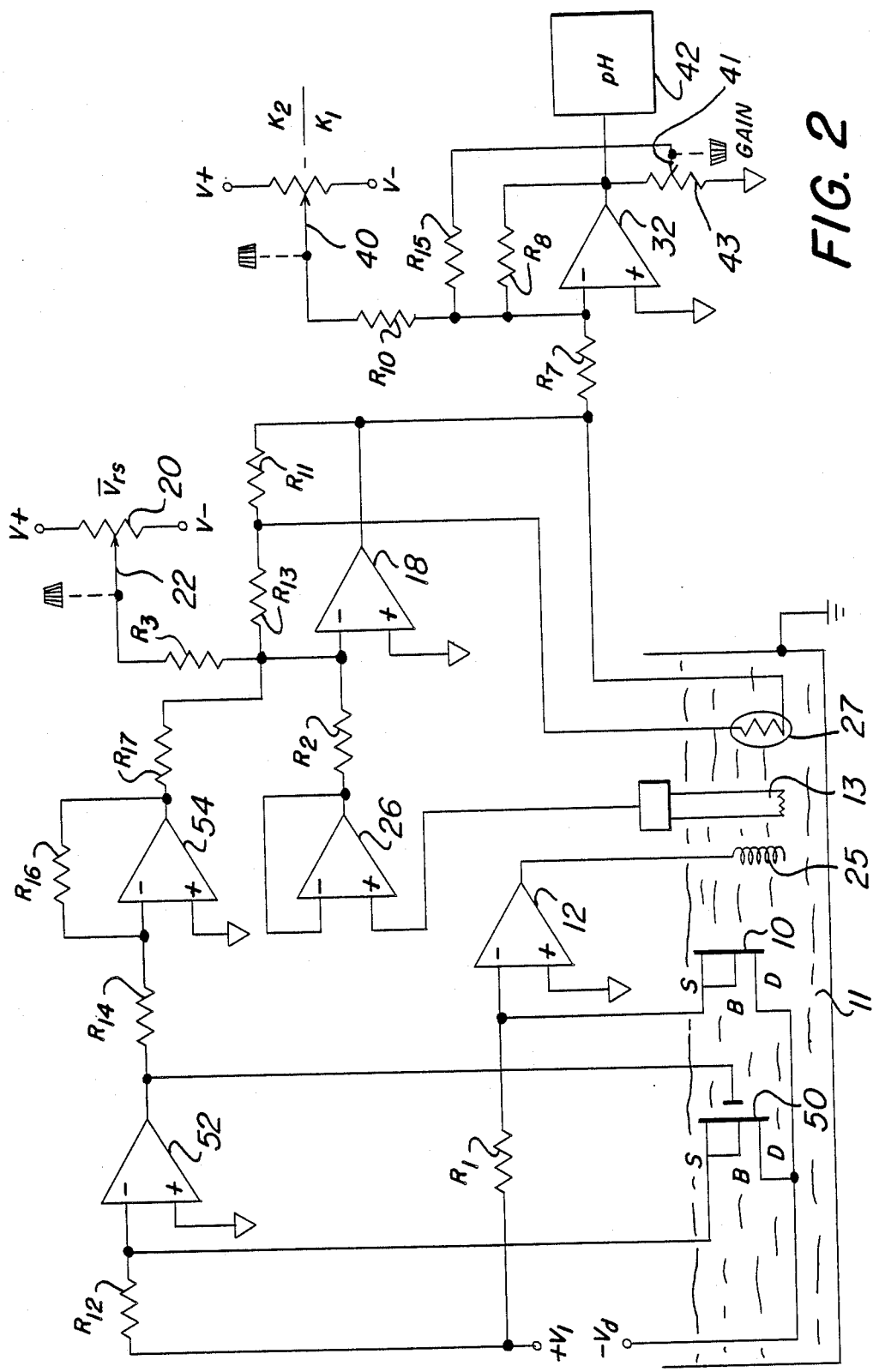
FIG. 2 is a circuit diagram which uses a differential ISFET/MOSFET pair with temperature compensation which utilizes a thermistor temperature sensor. The circuit also shows utilization of a counter electrode which will allow certain measurements which could not otherwise be made.

For the purpose of also illustrating the use of a counter electrode in the system, FIG. 2 is further modified from the arrangement of FIG. 1. The benefits of driving the ISFET with a counter electrode, and then taking the output from the reference electrode, as shown in the FIG. 2, are described in U.S. patent application Ser. No. 07/020,056. They have to do with preventing the adverse effects of stray parasitic currents. With the arrangement shown and with a high input impedance in the circuit connected to receive the output of the reference electrode, these effects can be prevented.

In addition to the use of a counter electrode, the circuit of FIG. 1 has been modified in FIG. 2 by the use of a negative temperature coefficient thermistor as the temperature sensor instead of an RTD, as shown in FIG. 1.

In FIG. 2 the amplifier 12 drives the counter electrode 25 so as to maintain the source of ISFET 10 at circuit common. The reference electrode 13 is then connected to the input of buffer amplifier 26, which is a high impedance input. The output of the buffer amplifier which is then fed as the input to amplifier 18, by way of resistor $R_2$, represents $V_{rs}$. Another input to amplifier 18 is that representing $\overline{V}_{rs}$ which is obtained from the tap 22 through resistor $R_3$, as in FIG. 1. In FIG. 2, there is an additional input to amplifier 18 which does not appear in FIG. 1. That input is the input supplied from MOSFET 50, which will be explained subsequently.

The RTD temperature sensor of FIG. 1 is replaced in FIG. 2 by a negative temperature coefficient thermistor 27 which is connected in shunt to one part of the feedback resistance for amplifier 18, namely resistor $R_{11}$. The other part of the feedback resistor for amplifier 18 is $R_{13}$. The values and the relationship between $R_{11}$ and $R_{13}$ are, of course, determined by the characteristic of thermistor 27.

The output of amplifier 18 provides the input to amplifier 32 through input resistor $R_7$. Amplifier 32 has other inputs including that from tap 40 through resistor $R_{10}$, as in FIG. 1. In addition another input is added from a tap 41 on potentiometer 43, which is supplied from the output of amplifier 32 through resistor $R_{15}$. Adjustment of the tap 41 will adjust the gain of amplifier 32 separately from the adjustment mentioned in FIG. 1. As shown, the output of amplifier 32 is a potential representative of the fully temperature compensated pH of the sample being measured, and will be indicated on the output device 42.

The MOSFET 50, as shown in FIG. 2, is connected for the appropriate biases by virtue of the connection of its drain to the voltage source $-V_d$ and the connection of its source to the voltage source $+V_1$ through resistor $R_{12}$, similar to the connections for the ISFET 10. The MOSFET source is then connected to the inverting input of operational amplifier 52 whose output is connected to the gate of the MOSFET so that the amplifier drives the MOSFET to hold its source at circuit common potential.

The output of the amplifier 52 provides the input to the inverting input of an operational amplifier 54. Amplifier 54 is connected to be a unity gain inverting amplifier by virtue of the values selected for input resistor $R_{14}$ and feedback resistor $R_{16}$. The output of amplifier 54 is then introduced as one of the inputs to the amplifier 18 by connection to the inverting input of that amplifier through resistor $R_{17}$. By virtue of these connections, the isopotential pH and voltage characteristics of the ISFET/NISFET pair will be constant from FET pair to FET pair because both will be at the temperature of the sample. Thus, there will be provided the desired accuracy for the pH measurement without the need of testing each ISFET during production in order to obtain a pH probe which can be interchanged with any other one without requiring a readjustment of the tap 22, as would be needed to accomodate different values of $\overline{V}_{rs}$.

It will be evident that while this description of the invention describes measuring pH, measurement of the ion activity, $a_i$, of other ions can be accomplished by designing the ISFET to be selective to the ion to be measured. The relationship described above for pH can be applied to the general case by substituting pIon for pH in the equations. Furthermore, the circuitry of FIGS. 1 and 2 can be modified to accomodate n-channel and p-channel devices of either enhancement or depletion mode characteristics by proper selection of circuit polarities and circuitry applicable to operation in the linear or non-linear FET regions. It will also be evident that many of the circuit elements shown in the drawings can be incorporated on the same chip as the ISFET, or the ISFET/NISFET pair, with all of the benefits that would normally be expected from the integration of those circuit elements with the elements of the probe itself.

What is claimed is:

1. Apparatus for producing a temperature compensated measurement of the activity of specific ions in an electrolyte sample comprising:
    a potentiometrically operated ISFET probe selectively responsive to said ions and operating with a constant drain-source voltage and drain-source current; and
    means for modifying the output of the ISFET probe in accordance with the expression $$p\text{Ion} = \frac{(V_{rs} - \overline{V}_{rs})}{K_1 T} - \frac{K_2}{K_1}$$

where $V_{rs}$ is the output of the ISFET probe; T is the absolute temperature of the sample; $K_1$ is the Nernst factor; and $\overline{V}_{rs}$ is the isopotential reference-to-source voltage; $K_2$ is a voltage temperature coefficient, not including in-situ or interfacial ionic temperature coefficients conventionally determined at the time of electrode standardization or calibration, whereby the modified output of the ISFET probe is indicative of a function of the ionic activity, pIon, of the sample.

2. Apparatus for determining the pIon activity of a sample, comprising:
   a potentiometrically operated ISFET probe for immersion in said sample, said ISFET producing a change in its output signal in response to changes in the ion activity of said sample;
   means for operating said ISFET at a constant drain-source voltage and a particular drain-source current which is independent of the characteristics of said ISFET
   subtracting means for subtracting from said ISFET output signal a signal representative of the isopotential voltage of the probe at said constant current;
   a temperature sensitive probe having a characteristic which is responsive to the temperature of the sample upon immersion in the sample;
   means for producing a modification of the output of said first subtracting means, said modification being in accordance with the product of the Nernst factor and the absolute temperature of the sample as represented by the temperature responsive characteristic of said temperature sensitive probe; and
   adding means for further modifying the modified output of the subtracting means by adding a quantity representative of the isopotential pIon value of the probe, whereby the output of the adding means is a signal indicative of the pIon value of the sample which is independent of changes in the temperature of the sample.

3. Apparatus in accordance with claim 2 in which said temperature sensitive probe is a resistance thermometer detector.

4. Apparatus in accordance with claim 2 in which said temperature sensitive probe is a negative temperature coefficient thermistor.

5. Apparatus for determining the pIon activity of a sample, comprising:
   a potentiometrically operated ISFET probe for immersion in said sample, said ISFET producing a change in its output signal in response to changes in the ion activity of said sample;
   means for operating said ISFET at a constant drain-source voltage and a particular drain-source current which is independent of the characteristics of said ISFET, said last named means including
   a voltage source connected to the drain of the ISFET,
   another voltage source connected to the source of the ISFET through a resistor, and
   an operational amplifier whose inverting input is connected to the source of the ISFET and whose noninverting input is connected to circuit common;
   a counter electrode immersed in the sample and driven by the output of said amplifier;
   a reference electrode immersed in said sample for supplying the output of the probe;
   subtracting means for subtracting from said ISFET output signal a signal representative of the isopotential voltage of the probe at said constant current;
   a temperature sensitive probe having a characteristic which is responsive to the temperature of the sample upon immersion in the sample;
   means for producing a modification of the output of said subtracting means, said modification being in accordance with the product of the Nernst factor and the absolute temperature of the sample as represented by the temperature responsive characteristic of said temperature sensitive probe; and
   adding means for further modifying the modified output of the subtracting means by adding a quantity representative of the isopotential pIon value of the probe, whereby the output of the adding means is a signal indicative of the pIon value of the sample which is independent of changes in the temperature of the sample.

6. Apparatus in accordance with claims 5 which further includes
   a NISFET constructed on the same substrate as the ISFET and simultaneously with the construction of said ISFET to form a pair therewith;
   an operational amplifier having its inverting input connected to the source of said NISFET and its noninverting input connected to circuit common with the amplifier output driving the NISFET to hold its source at circuit common; and
   means for subtracting the output of said last named operational amplifier from the output of said ISFET probe, whereby the difference between the ISFET's isopotential reference-to-source voltage and the NISFET's output voltage, extrapolated over temperature to 0° K., is maintained essentially constant from one pair to another.

7. Apparatus for determining the pIon activity of a sample, comprising:
   a potentiometrically operated ISFET probe for immersion in said sample, said ISFET producing a change in its output signal in response to changes in the ion activity of said sample;
   means for operating said ISFET at a constant drain-source voltage and a particular drain-source current which is independent of the characteristics of said ISFET, said last named means including
   a voltage source connected to the drain of the ISFET,
   another voltage source connected to the source of the ISFET through a fixed resistor,
   an operational amplifier whose inverting input is connected to the source of the ISFET and whose noninverting input is connected to circuit common; and
   an electrode immersed in the sample and driven by said operational amplifier so as to hold the source of the ISFET probe at circuit common;
   subtracting means for subtracting from said ISFET output signal a signal representative of the isopotential voltage of the probe at said constant current;
   a temperature sensitive probe having a characteristic which is responsive to the temperature of the sample upon immersion in the sample;
   means for producing a modification of the output of said subtracting means, said modification being in accordance with the product of the Nernst factor and the absolute temperature of the sample as represented by the temperature responsive characteristic of said temperature sensitive probe; and
   adding means for further modifying the modified output of the subtracting means by adding a quantity representative of the isopotential pIon value of the probe, whereby the output of the adding means is a signal indicative of the pIon value of the sample which is independent of changes in the temperature of the sample.

8. Apparatus in accordance with claims 7 which further includes
   a NISFET constructed on the same substrate as the ISFET and simultaneously with the construction of said ISFET to form a pair therewith;
   an operational amplifier having its inverting input connected to the source of said NISFET and its noninverting input connected to circuit common with the amplifier output driving the NISFET to hold its source at circuit common; and
   means for subtracting the output of said last named operational amplifier from the output of said ISFET probe, whereby the difference between the ISFET's isopotential reference-to-source voltage and the NISFET's output voltage, extrapolated over temperature to 0° K., is maintained essentially constant from one pair to another.

9. Apparatus as set forth in claim 7 in which
   said electrode is a reference electrode and the connection between the electrode and the amplifier provides the output of the ISFET probe.

10. Apparatus as set forth in claim 7 in which
    said electrode is a counter electrode and
    said probe further includes a reference electrode for providing the output of the probe.

11. A method for temperature compensating the output signal of a potentiometrically operated ISFET probe immersed in an electrolyte sample, said probe being selective of a specific ion to be measured in that sample and operating with a constant drain-source voltage and constant drain-source current, comprising the steps of
    providing a NISFET constructed on the same substrate as the ISFET and simultaneously with the construction of the ISFET and operated with a constant drain-source voltage and drain-source current;
    subtracting the output of said NISFET from the output of said ISFET to provide a difference signal;
    subtracting from said difference signal another signal representative of the isopotential voltage of the ISFET/NISFET pair;
    measuring the temperature of the sample;
    modifying the signal resulting from the last named subtraction by a factor inversely proportional to the product of the Nernst factor and the absolute temperature of the sample, as determined from said temperature measurement.

12. A method for temperature compensating over a full range of pIon values the output signal of a potentiometrically operated ISFET probe immersed in a sample, when the ISFET is operated at a preselected constant drain-source voltage and drain-source current whose values are selected independent of the variations in the characteristics of the ISFET from device to device and when the isopotential voltage of the ISFET at said constant current is known, comprising the steps of:
    decreasing the output signal obtained from the selected ISFET by an amount corresponding to said known isopotential voltage; and
    converting the decreased output signal to pIon values, said conversion being made in accordance with the Nernst factor and the absolute temperature of the sample.

13. A method for temperature compensating the output signals of interchangeble potentiometrically operated ISFET probes used to measure over a full range of values the pIon activity of a sample, comprising the steps of:
    operating the probe with a constant drain-source current and voltage without regard to which ISFET is being used;
    decreasing the output signal obtained during operation by an amount corresponding to the isopotential voltage of the ISFET at said constant current and voltage; and
    converting the decreased output signal to corresponding pIon values, said conversion being made in accordance with the Nernst factor and the absolute temperature of the sample.

14. The method of claim 13 which includes the step of
    determining the isopotential voltage of the ISFET by immersing the ISFET in a standard buffer solution,
    measuring the output of the immersed ISFET at two known temperatures and
    plotting the ISFET characteristics based on the known pIon of the buffer and the known value for the Nernst factor.

15. Apparatus for temperature compensating the output signal of a potentiometrically operated ISFET probe immersed in an electrolyte sample whose pIon value is to be measured over a full range of values, comprising:
    means for operating the ISFET probe at a constant drain-source voltage and a constant drain-source current whose values are independent of which ISFET is used;
    means for producing a modification of said output signal to reduce the magnitude of that signal by a value representative of the isopotential voltage of the probe at said constant current; and
    means for converting the modified output signal to pIon values, said conversion being made in accordance with the Nernst factor and the absolute temperature of the sample.

16. An ion activity monitoring device which comprises:
    an ion-sensitive field-effect transistor for detecting the activity of ions in a liquid medium of interest, and developing an ion activity signal indicative thereof;
    a temperature sensor for detecting the temperature of the liquid medium of interest and developing a temperature signal indicative thereof;
    a circuit for maintaining constant the drain-source voltage and the drain-source current of the ion-sensitive field-effect transistor, said current being maintained constant at a value independent of the variations in the characteristics of said ion-sensitive field-effect transistor from device to device; and
    a processing circuit responsive to both the ion activity signal from the ion-sensitive field-effect transistor and the temperature signal from the temperature sensor, for calculating the concentration of the ions in the liquid medium of interest, said processing circuit including,
    compensating means for effecting an adjustment to the ion activity signal from the ion-sensitive field-effect transistor by subtracting the magnitude of the isopotential value for the ion activity signal, and
    compensating means for adjusting the sensitivity of the monitoring device to the ion activity, based on the temperature signal.

17. The device of claim 16 which includes means for offsetting said monitoring device in accordance with the magnitude of the isopotential value for the ion activity.

18. Apparatus for determining a temperature independent value for the activity of a specific ion in an electrolyte sample, comprising:
   an ISFET probe immersed in said sample and producing an output voltage which varies with variations in said ion activity, said probe being operated at a constant drain-source voltage and a constant drain-source current, both of which are selected independent of the ISFET's particular isopotential pIon value at said constant current;
   means for decreasing said output voltage by an amount equal to the isopotential voltage of said probe at said constant current; and
   means for converting the resulting decreased voltage magnitude to pIon values, said conversion being in accordance with the Nernst factor times the absolute temperature of the sample.

19. Apparatus as set forth in claim 18 which includes means for offsetting the converted result in accordance with the isopotential pIon value.

20. The method for temperature compensating a measurement of the pIon value of an electrolyte sample with an ISFET operating at any selected constant drain-source current and drain-source voltage, comprising the steps of:
   providing at least one standard electrolyte sample of any known pIon value;
   determining the isopotential voltage of said ISFET at said constant current by
   measuring the output voltage of said ISFET when it is immersed in one of said standard samples at a first temperature,
   measuring the output voltage of said ISFET when it is immersed in one of said standard samples at a second temperature, and
   extrapolating from said measured output voltages and the known values of absolute temperatures at which the measurements were made, the value of the isopotential voltage for said ISFET;
   immersing said ISFET in the unknown sample to produce an output voltage therefrom in response to the pIon value of the unknown;
   decreasing the ISFET output voltage due to said unknown by the value of said isopotential voltage; and
   converting the decreased output to pIon terms in accordance with the product of said Nernst factor and the absolute temperature of said unknown sample.

* * * * *